(12) United States Patent
Mizoguchi et al.

(10) Patent No.: US 10,759,755 B2
(45) Date of Patent: Sep. 1, 2020

(54) BISPHENOL COMPOUND AND AROMATIC POLYCARBONATE

(71) Applicant: Honshu Chemical Industry Co., Ltd., Chuo-ku, Tokyo (JP)

(72) Inventors: Shun Mizoguchi, Wakayama (JP); Xuwang Lu, Wakayama (JP)

(73) Assignee: Honshu Chemical Industry Co., Ltd., Tokyo (JP)

( * ) Notice: Subject to any disclaimer, the term of this patent is extended or adjusted under 35 U.S.C. 154(b) by 84 days.

(21) Appl. No.: 16/068,310

(22) PCT Filed: Dec. 16, 2016

(86) PCT No.: PCT/JP2016/087479
§ 371 (c)(1),
(2) Date: Jul. 5, 2018

(87) PCT Pub. No.: WO2017/119262
PCT Pub. Date: Jul. 13, 2017

(65) Prior Publication Data
US 2019/0047954 A1    Feb. 14, 2019

(30) Foreign Application Priority Data

Jan. 8, 2016 (JP) .................. 2016-002849

(51) Int. Cl.
*C08G 64/12* (2006.01)
*C07D 209/34* (2006.01)
*C08G 64/30* (2006.01)

(52) U.S. Cl.
CPC ........... *C07D 209/34* (2013.01); *C08G 64/12* (2013.01); *C08G 64/307* (2013.01)

(58) Field of Classification Search
CPC ..................................... C08G 64/12
USPC ....................................... 528/228
See application file for complete search history.

(56) References Cited

U.S. PATENT DOCUMENTS

2008/0081896 A1* 4/2008 Heuer .................. C08G 64/04
528/196

FOREIGN PATENT DOCUMENTS

| JP | 51 92893 | 8/1976 |
|---|---|---|
| JP | 1988 108023 | 5/1988 |
| JP | 1989 156323 | 6/1989 |
| JP | 1996 183853 | 7/1996 |
| JP | 1998 114695 | 5/1998 |
| JP | 2002 179650 | 6/2002 |
| JP | 2006 508893 | 3/2006 |
| JP | 2010 505011 | 2/2010 |
| JP | 2011 246583 | 12/2011 |

OTHER PUBLICATIONS

International Search Report, dated Feb. 21, 2017, in corresponding international patent application No. PCT/JP2016/087479.
Hernandez, Novel, Metal-Free, Superacid-Catalyzed "Click" Reactions of Isatins with Linear, Nonactivated, Multiring Aromatic Hydrocarbons, Macromolecules, Aug. 2, 2010, pp. 6968-6979, vol. 43, No. 17.
Notification concerning Transmittal of International Preliminary Report on Patentability dated Jul. 19, 2018 in International Application No. PCT/JP2016/087479.
Notification of Transmittal of Translation of the International Preliminary Report on Patentability dated Jul. 19, 2018 in International Application No. PCT/JP2016/087479.

* cited by examiner

*Primary Examiner* — Duc Truong
(74) *Attorney, Agent, or Firm* — Knobbe Martens Olson & Bear LLP

(57) ABSTRACT

The present invention addresses the problem of providing: a novel bisphenol compound having an indoline skeleton; and a novel aromatic polycarbonate which uses this bisphenol compound as a starting material dihydroxy compound. The above-described problem is able to be solved by an aromatic polycarbonate that contains a repeating unit represented by general formula (2).

[Chemical Formula 2]

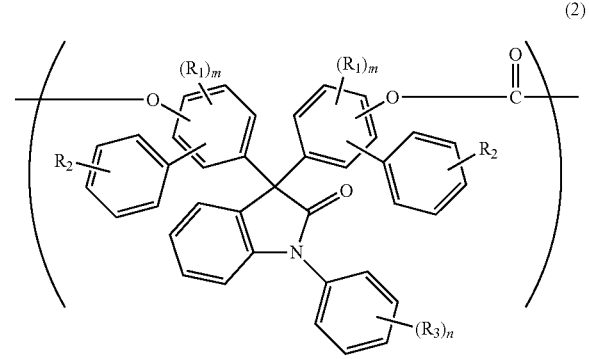

3 Claims, No Drawings

BISPHENOL COMPOUND AND AROMATIC POLYCARBONATE

TECHNICAL FIELD

The present invention relates to a novel bisphenol compound and a novel aromatic polycarbonate including the same. More specifically, the present invention relates to a bisphenol compound having an indoline skeleton, which is suitable as a raw material for aromatic polycarbonate oligomers or resins, and an aromatic polycarbonate that includes this bisphenol compound as a raw material dihydroxy compound.

BACKGROUND ART

Conventionally, bisphenols have been used as raw materials for thermoplastic synthetic resins such as polycarbonate resins, thermosetting resins such as epoxy resins, antioxidants, heat sensitive recording bodies, photosensitive resists, and the like. In recent years, the performances required for these bisphenols have been increasing more and more. Among them, some bisphenols having an indoline skeleton excellent in mechanical strength, optical properties and the like when made into an aromatic polycarbonate have been known (Patent Literatures 1 and 2). For example, 3,3-bis(4-hydroxyphenyl)-1-phenyl-1H-indol-2-one has been known as a raw material bisphenol for aromatic polycarbonate having a relatively high glass transition temperature and improved adhesion to metals (Patent Literature 2). However, while the compound has high heat resistance when made into an aromatic polycarbonate, the compound has a high melting point, so that the operability is poor and further improvement in optical properties is also required.

CITATION LIST

Patent Literatures

Patent Literature 1: JP 2002-179650 A
Patent Literature 2: JP 2010-505011 A

SUMMARY OF THE INVENTION

Technical Problems

The present invention has been made in view of the above-mentioned circumstances, and an object of the present invention is to provide a novel bisphenol compound having an indoline skeleton with high heat resistance, high refractive index and low melting point, and provide a novel aromatic polycarbonate that includes this bisphenol compound as a raw material dihydroxy compound.

Solution to Problems

As a result of intensive studies to solve the above-mentioned problems, the present inventors have found that bisphenol having N-phenyl-substituted isatin as a skeleton and having a phenyl substituent added to a hydroxyphenyl group has high heat resistance and high refractive index as compared with conventionally known 3,3-bis(4-hydroxyphenyl)-1-phenyl-1H-indol-2-one, and accomplished the present invention.

The present invention is as follows.
1. A bisphenol compound represented by general formula (1) below:

[Chemical Formula 1]

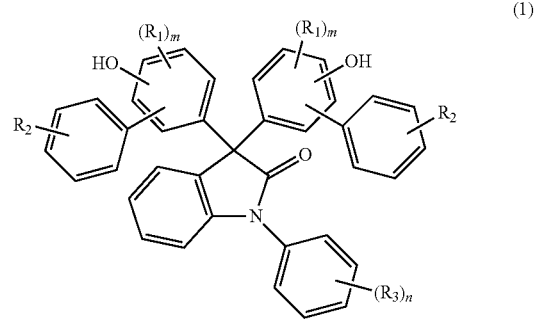

(1)

wherein $R_1$s each independently represent an alkyl group having 1 to 8 carbon atoms, an alkoxy group having 1 to 8 carbon atoms, a phenyl group or a halogen atom, $R_2$s each independently represent a hydrogen atom, an alkyl group having 1 to 8 carbon atoms, an alkoxy group having 1 to 8 carbon atoms or a halogen atom, $R_3$ represents an alkyl group having 1 to 8 carbon atoms, an alkoxy group having 1 to 8 carbon atoms or a halogen atom, m represents an integer of 0 to 2, and n represents an integer of 0 to 2, provided that when m is 2, $R_1$s may be the same as or different from each other, and when n is 2, $R_3$s may be the same as or different from each other.

2. An aromatic polycarbonate comprising a repeating unit represented by general formula (2) below:

[Chemical Formula 2]

(2)

wherein $R_1$s each independently represent an alkyl group having 1 to 8 carbon atoms, an alkoxy group having 1 to 8 carbon atoms, a phenyl group or a halogen atom, $R_2$s each independently represent a hydrogen atom, an alkyl group having 1 to 8 carbon atoms, an alkoxy group having 1 to 8 carbon atoms or a halogen atom, $R_3$ represents an alkyl group having 1 to 8 carbon atoms, an alkoxy group having 1 to 8 carbon atoms or a halogen atom, m represents an integer of 0 to 2, and n represents an integer of 0 to 2, provided that when m is 2, $R_1$s may be the same as or different from each other, and when n is 2, $R_3$s may be the same as or different from each other.

3. The aromatic polycarbonate comprising the repeating unit represented by general formula (2) according to 2, which is obtained from the bisphenol compound represented by general formula (1) according to 1 and diphenyl carbonate.

Advantageous Effects of Invention

Since the bisphenol compound according to the present invention has a low melting point, it is particularly excellent in operability during polymerization in the production of polycarbonate. The compound itself has a low melting point; however, it has high heat resistance and further has a high refractive index, so that excellent effects as a polycarbonate raw material for optical materials can be expected.

Further, since the bisphenol compound according to the present invention has a plurality of reactive phenolic hydroxyl groups, excellent effects can be expected as it is or as a derivative, for example, as various resin raw materials of an epoxy resin obtained by reacting the bisphenol compound with epichlorohydrin, an oxetane resin obtained by reacting the bisphenol compound with 2-(3-oxetanyl)butyl tosylate, a resin obtained by reacting the bisphenol compound with acrylic acid (or methacrylic acid), furthermore, polyester, polyarylate, polyether ether ketone, polysulfone, novolac resin, resole resin and the like, and as an i-line resist additive, a developer, an antioxidant, or the like.

Furthermore, the aromatic polycarbonate of the present invention includes the bisphenol with a low melting point according to the present invention as the raw material dihydroxy compound monomer, so that it has good operability and has little fear of coloration or monomer decomposition when polycarbonate is produced by melt transesterification method or solid phase polymerization. Thus, the obtained polycarbonate is expected to have high purity, high heat resistance and high refractive index, and excellent effects can be expected particularly for polycarbonate for optical materials.

DESCRIPTION OF EMBODIMENTS

Hereinafter, the present invention will be described in detail.

The bisphenol compound of the present invention is represented by general formula (1) below:

[Chemical Formula 3]

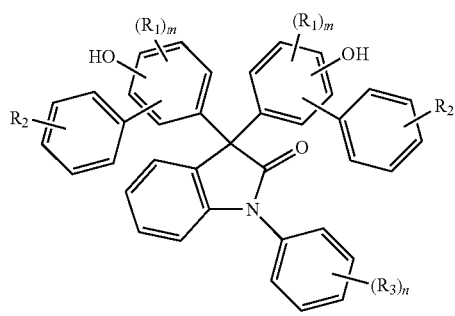

(1)

wherein $R_1$s each independently represent an alkyl group having 1 to 8 carbon atoms, an alkoxy group having 1 to 8 carbon atoms, a phenyl group or a halogen atom, $R_2$s each independently represent a hydrogen atom, an alkyl group having 1 to 8 carbon atoms, an alkoxy group having 1 to 8 carbon atoms or a halogen atom, $R_3$ represents an alkyl group having 1 to 8 carbon atoms, an alkoxy group having 1 to 8 carbon atoms or a halogen atom, m represents an integer of 0 to 2, and n represents an integer of 0 to 2, provided that when m is 2, $R_1$s may be the same as or different from each other, and when n is 2, $R_3$s may be the same as or different from each other.

In general formula (1), each of $R_1$s is independently an alkyl group having 1 to 8 carbon atoms, an alkoxy group having 1 to 8 carbon atoms, a phenyl group or a halogen atom, and when $R_1$ is an alkyl group having 1 to 8 carbon atoms, the alkyl group is preferably a linear or branched alkyl group having 1 to 4 carbon atoms, and specific examples thereof include a methyl group, an ethyl group, a n-propyl group, an isopropyl group, an isobutyl group, and the like. The alkyl group may have, for example, a substituent such as a phenyl group or an alkoxy group as long as the effect of the present invention is not impaired.

Also, when $R_1$ is an alkoxy group having 1 to 8 carbon atoms, the alkoxy group is preferably a linear or branched alkoxy group having 1 to 4 carbon atoms, and specific examples thereof include a methoxy group, an ethoxy group, a n-propoxy group, an isopropoxy group, and the like. The alkoxy group may have, for example, a substituent such as a phenyl group or an alkoxy group as long as the effect of the present application is not impaired.

Moreover, when $R_1$ is a phenyl group, the phenyl group may have, for example, a substituent such as an alkyl group or an alkoxy group as long as the effect of the present application is not impaired.

Further, when $R_1$ is a halogen atom, specific examples of the halogen atom include a fluorine atom, a chlorine atom, a bromine atom, and an iodine atom.

$R_1$ is preferably a methyl group or a phenyl group.

Each of $R_2$s is independently a hydrogen atom, an alkyl group having 1 to 8 carbon atoms, an alkoxy group having 1 to 8 carbon atoms or a halogen atom, $R_3$ is an alkyl group having 1 to 8 carbon atoms, an alkoxy group having 1 to 8 carbon atoms or a halogen atom, and when $R_2$ and $R_3$ are each an alkyl group having 1 to 8 carbon atoms, the preferred groups and specific examples are the same as those for $R_1$, and similarly, when $R_2$ and $R_3$ are each an alkoxy group having 1 to 8 carbon atoms or a halogen atom, the preferred groups and specific examples are the same as those for $R_1$. $R_2$ is preferably a hydrogen atom or a methyl group, and $R_3$ is preferably a methyl group.

Also, in general formula (1), m is 0, 1 or 2, and preferably 0 or 1, and n is 0, 1 or 2, preferably 0 or 1, and particularly preferably 0.

In general formula (1), as to the substitution positions of the hydroxy group substituted for the phenyl group directly bonded to the carbon atom at the 3-position of the indoline skeleton, the phenyl group, and $R_1$, first, the hydroxy group is preferably substituted at the 4- or 2-position, and more preferably substituted at the 4-position with respect to the phenyl carbon atom directly bonded to the carbon atom at the 3-position of the indoline skeleton.

Moreover, the phenyl group is preferably substituted at the o-position or the p-position with respect to the hydroxy group, and when the hydroxy group is substituted at the 4-position with respect to the phenyl carbon atom directly bonded to the carbon atom at the 3-position of the indoline skeleton, the phenyl group is preferably substituted at the 3- or 5-position, and when the hydroxy group is substituted at the 2-position, the phenyl group is preferably substituted at the 3- or 5-position.

Further, in general formula (1), $R_1$ is preferably substituted at the o-position or the p-position with respect to the hydroxy group, and when the hydroxy group is substituted at the 4-position and the phenyl group is substituted at the 3-position with respect to the phenyl carbon atom directly bonded to the carbon atom at the 3-position of the indoline skeleton, $R_1$ is preferably substituted at the 5-position, when the hydroxy group is substituted at the 2-position and the phenyl group is substituted at the 3-position, $R_1$ is preferably substituted at the 5-position, and when the hydroxy group is substituted at the 2-position and the phenyl group is substituted at the 5-position, $R_1$ is preferably substituted at the 3-position.

Furthermore, the substitution position of $R_1$ when m is 2 is preferably such that the hydroxyl group is substituted at the 4-position, the phenyl group is substituted at the 3-position, and $R_1$ is substituted at the 5-position and the 6-position, or the hydroxyl group is substituted at the 4-position, the phenyl group is substituted at the 3-position, and $R_1$ is substituted at the 2-position and the 5-position, with respect to the phenyl carbon atom directly bonded to the carbon atom at the 3-position of the indoline skeleton.

Therefore, the bisphenol compound represented by general formula (1) is preferably represented by general formula (3) below:

[Chemical Formula 4]

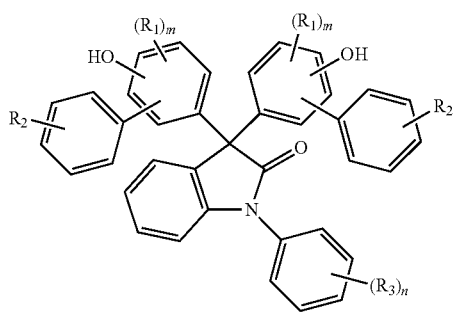

(3)

wherein $R_1$, $R_2$, $R_3$, m and n are the same as those in general formula (1).

In the bisphenol compound represented by general formula (3), when m is 1, the substitution position of $R_1$ is preferably the 5-position with respect to the phenyl carbon atom directly bonded to the carbon atom at the 3-position of the indoline skeleton, and when m is 2, the substitution position of $R_1$ is preferably the 5-position and the 6-position, or the 2-position and the 5-position, with respect to the phenyl carbon atom directly bonded to the carbon atom at the 3-position of the indoline skeleton.

Specific examples of the bisphenol compound represented by general formula (1) of the present invention include 3,3-bis(4-hydroxy-3-phenylphenyl)-1-phenyl-1H-indol-2-one

[Chemical Formula 5]

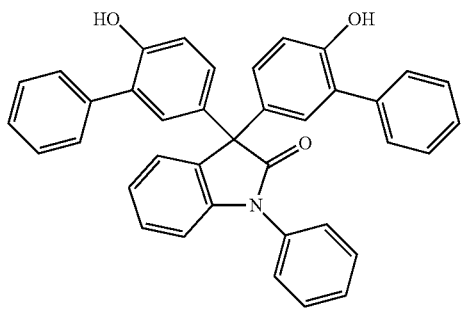

(4)

3,3-bis(4-hydroxy-5-methyl-3-phenylphenyl)-1-phenyl-1H-indol-2-one
3,3-bis(5-ethyl-4-hydroxy-3-phenylphenyl)-1-phenyl-1H-indol-2-one
3,3-bis(4-hydroxy-3,5-diphenylphenyl)-1-phenyl-1H-indol-2-one
3,3-bis(4-hydroxy-5-methoxy-3-phenylphenyl)-1-phenyl-1H-indol-2-one
3,3-bis(4-hydroxy-5,6-dimethyl-3-phenylphenyl)-1-phenyl-1H-indol-2-one
3,3-bis(4-hydroxy-2,5-dimethyl-3-phenylphenyl)-1-phenyl-1H-indol-2-one
3,3-bis(4-hydroxy-3-(4-methylphenyl)phenyl)-1-phenyl-1H-indol-2-one
3,3-bis(4-hydroxy-3-(3-methylphenyl)phenyl)-1-phenyl-1H-indol-2-one
3,3-bis(2-hydroxy-5-phenylphenyl)-1-phenyl-1H-indol-2-one
3,3-bis(2-hydroxy-3-phenylphenyl)-1-phenyl-1H-indol-2-one
3,3-bis(4-hydroxy-3-phenylphenyl)-1-(4-methylphenyl)-1H-indol-2-one
3,3-bis(4-hydroxy-3-phenylphenyl)-1-(2-methylphenyl)-1H-indol-2-one
3,3-bis(4-hydroxy-3-phenylphenyl)-1-(4-methoxyphenyl)-1H-indol-2-one
and the like.

The bisphenol represented by general formula (1) of the present invention is not particularly limited as to its production method, and a known method for producing bisphenols is applicable; however, it can be preferably obtained by using an N-phenylisatin compound represented by general formula (5) below and a phenylphenol compound represented by general formula (6) below as raw materials, and reacting these compounds in the presence of an acid catalyst:

[Chemical Formula 6]

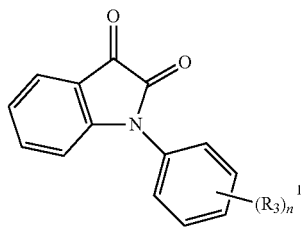

(5)

wherein $R_3$ and n are the same as those in general formula (1).

Preferred examples and specific examples of $R_3$ and n are also the same as those of general formula (1).

Specific examples of the N-phenylisatin compound represented by general formula (5) include
1-phenyl-1H-indole-2,3-dione
1-(4-methylphenyl)-1H-indole-2,3-dione
1-(2-methylphenyl)-1H-indole-2,3-dione
1-(4-methoxyphenyl)-1H-indole-2,3-dione
and the like.

Also,

[Chemical Formula 7]

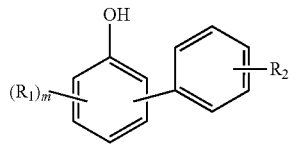

(6)

wherein $R_1$, $R_2$, and m are the same as those in general formula (1).

Preferred examples and specific examples of $R_1$ and $R_2$ are also the same as those of general formula (1).

Specific examples of the phenylphenol compound represented by general formula (6) include
2-phenylphenol
6-methyl-2-phenylphenol
6-ethyl-2-phenylphenol
2,6-diphenylphenol
6-methoxy-2-phenylphenol
5,6-dimethyl-2-phenylphenol
3,6-dimethyl-2-phenylphenol
2-(4-methylphenyl)phenylphenol
2-(3-methylphenyl)phenylphenol
and the like.

In the production method in which the N-phenylisatin compound and the phenylphenol compound described above are reacted with each other in the presence of an acid catalyst, first, the N-phenylisatin compound and the phenylphenol compound are reacted with each other in the presence of an acid catalyst, and the obtained reaction mixture is neutralized with alkali, then crystallized and filtered according to a known method, to obtain a primary crystallization crude product.

In the reaction, the charged molar ratio of the phenylphenol compound to the N-phenylisatin compound is not particularly limited as long as it is greater than or equal to the theoretical value (2.0); however the phenylphenol compound is usually used in 2.5 times or more, preferably in the range of 2.5 to 20 times, and particularly preferably in the range of 3 to 10 times as large as the amount of the N-phenylisatin compound. Examples of the acid catalyst include inorganic acids such as hydrochloric acid, hydrogen chloride gas, 60 to 98% sulfuric acid and 85% phosphoric acid; organic acids such as p-toluenesulfonic acid, methanesulfonic acid, oxalic acid, formic acid, trichloroacetic acid and trifluoroacetic acid; solid acids such as heteropolyacids; and the like. Preferably, the acid catalyst is hydrogen chloride gas. While the preferred amount of the acid catalyst to be used is different depending on the reaction conditions, for example, in the case of hydrogen chloride gas, it is preferable that the air in the reaction system is replaced with an inert gas such as nitrogen gas, then hydrogen chloride gas is blown into the reaction system, and the concentration of the hydrogen chloride gas in the gas phase in a reaction vessel is set to 75 to 100% by volume to increase the concentration of hydrogen chloride in the reaction solution to the saturated concentration. In the case of 35% hydrochloric acid, it is used in the range of 5 to 70 parts by weight, preferably in the range of 10 to 40 parts by weight, and more preferably in the range of 20 to 30 parts by weight based on 100 parts by weight of the phenylphenol compound.

In the reaction, a co-catalyst may be used as necessary, together with the acid catalyst. For example, when hydrogen chloride gas is used as a catalyst, the reaction speed can be accelerated by using thiols as a co-catalyst. Examples of the thiols include alkyl mercaptans and mercaptocarboxylic acids, and are preferably alkyl mercaptans having 1 to 12 carbon atoms and mercaptocarboxylic acids having 1 to 12 carbon atoms. Examples thereof include methyl mercaptan, ethyl mercaptan, n-octyl mercaptan, n-lauryl mercaptan, and the like, alkali metal salts such as sodium salts of these compounds, thioacetic acid, β-mercaptopropionic acid, and the like. These may be used alone or in combination of two or more kinds thereof.

The amount of the thiols to be used as a co-catalyst is usually in the range of 1 to 30% by mol, and preferably in the range of 2 to 10% by mol based on the raw material N-phenylisatin compound.

In the reaction, a reaction solvent is not required to be used unless the melting points of the raw materials N-phenylisatin compound and phenylphenol compound are low and there is no problem in operability; however, a reaction solvent may be used for reasons such as operability during industrial production and improvement in reaction speed. The reaction solvent is not particularly limited as long as it is not distilled from the reactor at the reaction temperature and is inert to the reaction, and examples thereof include aromatic hydrocarbons such as toluene and xylene, aliphatic alcohols such as methanol, n-propyl alcohol and isobutyl alcohol, aliphatic hydrocarbons such as hexane, heptane and cyclohexane, carboxylic acid esters such as ethyl acetate and butyl acetate, and mixtures thereof. Among them, aliphatic alcohols are preferably used.

In addition, a small amount of water may be added as necessary to promote the reaction of the acid catalyst by lowering the freezing point of the phenylphenol compound. In particular, in the case where the acid catalyst is hydrogen chloride gas, water is preferable for promoting absorption of the hydrogen chloride gas as the catalyst. In the case of adding water, the addition amount thereof is preferably in the range of 0.5 to 5.0 parts by weight based on 100 parts by weight of the phenylphenol compound.

The reaction temperature is usually in the range of 10 to 60° C., and preferably 25 to 50° C. The reaction pressure is usually set under normal pressure; however depending on the boiling point of the organic solvent that may be used, the reaction may be carried out under pressure or reduced pressure so that the reaction temperature falls within the above range. When the reaction is carried out under such conditions, the reaction is usually completed in about 1 to 30 hours.

The end point of the reaction can be confirmed by liquid chromatography or gas chromatography analysis. It is preferable that the time point at which the unreacted N-phenylisatin compound disappears and no increase in an object substance is observed is taken as the end point of the reaction.

The reaction yield based on the phenylphenol compound is usually about 75 to 95% by mol.

After the completion of the reaction, an alkaline solution such as aqueous ammonia or an aqueous sodium hydroxide solution is added to the obtained reaction mixture to neutralize the acid catalyst, so that a reaction mixture containing the bisphenol represented by general formula (1) according to the present invention is obtained.

As a method for separating and purifying the object substance from the reaction mixture, a known method can be used. For example, the neutralized reaction mixture is directly cooled or the neutralized reaction mixture is once heated to be made into a homogeneous solution, followed by cooling, or the neutralized reaction mixture is added with a crystallization solvent such as methanol, then the obtained solution is cooled to precipitate crystals and the precipitated crystal is separated by filtration, whereby a crude or high purity object substance can be obtained.

The objective bisphenol thus obtained as above may be further purified as necessary to obtain a high purity product. In particular, when the bisphenol is used as a raw material dihydroxyphenol for polycarbonate, it is preferable to make the bisphenol into a high purity product. For example, the crystals of the obtained object substance are again dissolved in an appropriate solvent, for example, an aromatic solvent such as toluene or an aliphatic ketone solvent such as methyl ethyl ketone, and then a crystallization solvent such as methanol or water is added thereto, and the mixture is cooled again, crystallized, filtered, and dried. Alternatively, instead of the crystallization operation, it is also possible to obtain a high purity product of the object substance by concentrating the reaction solvent and the like from the reaction mixture under reduced pressure, after the completion of the reaction, and purifying the residue by column chromatography or the like.

Next, a novel aromatic polycarbonate of the present invention in which the bisphenol represented by general formula (1) is used as a raw material aromatic dihydroxy compound will be described.

The aromatic polycarbonate of the present invention is an aromatic polycarbonate including a repeating unit represented by general formula (2) below:

[Chemical Formula 8]

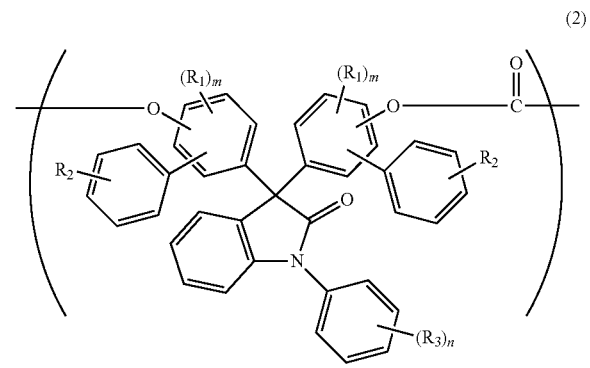

(2)

wherein $R_1$s each independently represent an alkyl group having 1 to 8 carbon atoms, an alkoxy group having 1 to 8 carbon atoms, a phenyl group or a halogen atom, $R_2$s each independently represent a hydrogen atom, an alkyl group having 1 to 8 carbon atoms, an alkoxy group having 1 to 8 carbon atoms or a halogen atom, $R_3$ represents an alkyl group having 1 to 8 carbon atoms, an alkoxy group having 1 to 8 carbon atoms or a halogen atom, m represents an integer of 0 to 2, and n represents an integer of 0 to 2, provided that when m is 2, $R_1$s may be the same as or different from each other, and when n is 2, $R_3$s may be the same as or different from each other.

In general formula (2), preferred examples and specific examples of the substituents represented by $R_1$, $R_2$ and $R_3$ and the definitions of the number of substitutions represented by m and n and preferred substitution positions are the same as those in general formula (1).

Accordingly, an aromatic polycarbonate including a preferable repeating unit in the aromatic polycarbonate including the repeating unit represented by general formula (2) is represented by general formula (7) below:

[Chemical Formula 9]

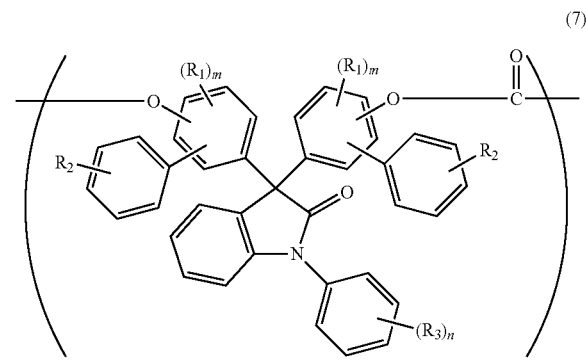

(7)

wherein $R_1$, $R_2$, $R_3$, m and n are the same as those in general formula (2).

The aromatic polycarbonate including the repeating unit represented by general formula (2) of the present invention is not particularly limited in its production method, and any conventionally known method can be used. Specific examples thereof include an interfacial polymerization method, a melt transesterification method (sometimes referred to as a melt polycondensation method), a solid phase polymerization method, a ring-opening polymerization method of a cyclic carbonate compound, a pyridine method, and the like. Among them, an interfacial polymerization method using an aromatic dihydroxy compound and a carbonate precursor as raw materials, and a melt transesterification method are preferable, and in particular, a production method by melt polycondensation of the bisphenol compound represented by general formula (1) and a carbonic acid ester such as diphenyl carbonate in the presence of a transesterification catalyst is preferable.

As the aromatic dihydroxy compound used as a raw material of the aromatic polycarbonate according to the present invention, other dihydroxy compounds such as bisphenol A other than the bisphenol compound represented by general formula (1) can be used as copolymerization raw materials within a range not disturbing the effect of the present invention.

In the case of using a copolymerization raw material, the proportion of the dihydroxy compound copolymerization raw material other than the bisphenol compound represented by general formula (1) mainly used in the total dihydroxy compounds is not particularly limited as long as the dihydroxy compound copolymerization raw material does not disturb the effect of the aromatic polycarbonate of the present invention, and the proportion is preferably in the range of 0 to 20% by mol, more preferably in the range of 0 to 10% by mol, further preferably in the range of 0 to 5% by mol, and particularly preferably in the range of 0 to 2% by mol.

The melt transesterification method for producing the aromatic polycarbonate including the repeating unit represented by general formula (2) of the present invention by melt polycondensation will be described in more detail. Here, as the melt transesterification method, a conventionally known method can be used.

For example, the reaction for obtaining the aromatic polycarbonate according to the present invention is shown by the reaction formula below when a raw material aromatic dihydroxy compound is 3,3-bis(4-hydroxy-3-phenylphenyl)-1-phenyl-1H-indol-2-one and a raw material carbonate diester is diphenyl carbonate.

[Chemical Formula 10]

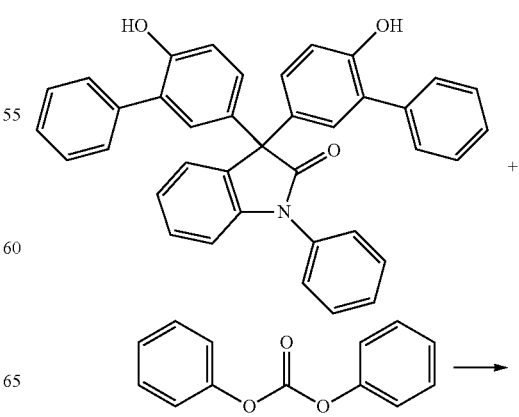

-continued

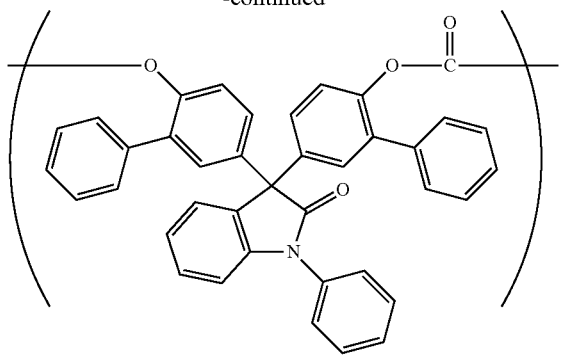

The melt transesterification reaction is carried out by stirring an aromatic dihydroxy compound and a carbonate diester in the presence of a catalyst while heating under an atmospheric pressure or reduced pressure inert gas atmosphere to distill phenol to be formed.

Specific examples of the carbonate diester to be reacted with the aromatic dihydroxy compound include diaryl carbonates such as diphenyl carbonate, ditolyl carbonate and bis(m-cresyl) carbonate; dialkyl carbonates such as dimethyl carbonate, diethyl carbonate, and dicyclohexyl carbonate; alkylaryl carbonates and divinyl carbonate such as methyl phenyl carbonate, ethyl phenyl carbonate and cyclohexyl phenyl carbonate; dialkenyl carbonates such as diisopropenyl carbonate and dipropenyl carbonate; and the like. Preferred is diaryl carbonate, and particularly preferred is diphenyl carbonate.

It is usually possible to obtain an aromatic polycarbonate in which the desired molecular weight and amount of terminal hydroxyl groups are adjusted by adjusting the mixing ratio of the aromatic dihydroxy compound to the carbonate diester and the degree of pressure reduction during the transesterification reaction.

The mixing ratio of the aromatic dihydroxy compound to the carbonate diester for obtaining the aromatic polycarbonate according to the present invention is usually 0.5 to 1.5 mol times, and preferably 0.6 to 1.2 mol times per mole of the aromatic dihydroxy compound.

In the melt transesterification reaction, a transesterification catalyst is used to increase the reaction speed, as necessary. The transesterification catalyst is not particularly limited, and examples thereof include known transesterification catalysts such as alkali metal compounds of inorganic alkali metal compounds such as hydroxides, carbonates and hydrogen carbonate compounds of lithium, sodium and cesium, and organic alkali metal compounds such as alcoholates and organic carboxylic acid salts; alkaline earth metal compounds of inorganic alkaline earth metal compounds such as hydroxides and carbonates of beryllium and magnesium, and organic alkaline earth metal compounds such as alcoholates and organic carboxylic acid salts; basic boron compounds such as sodium salts, calcium salts and magnesium salts of tetramethylboron, tetraethylboron, butyltriphenylboron, and the like; basic phosphorus compounds of trivalent phosphorus compounds such as triethylphosphine and tri-n-propylphosphine, and quaternary phosphonium salts derived from these compounds; basic ammonium compounds such as tetramethylammonium hydroxide, tetraethylammonium hydroxide, and tetrabutylammonium hydroxide, and amine compounds such as 4-aminopyridine, 2-dimethylaminoimidazole, and aminoquinoline; and the like.

Among them, alkali metal compounds are preferable, and cesium compounds such as cesium carbonate and cesium hydroxide are particularly preferable.

The amount of the catalyst to be used is in the range that the catalyst residue does not cause quality problems in the polycarbonate produced, and cannot be indiscriminately described because the preferable addition amount is different depending on the type of the catalyst; however, it is roughly, for example, usually 0.05 to 100 μmol, preferably 0.08 to 50 μmol, more preferably 0.1 to 20 μmol, and further preferably 0.1 to 5 μmol based on 1 mol of the bisphenol compound. The catalyst may be added as it is or dissolved in a solvent to be added, and the solvent is preferably a solvent that does not affect the reaction, such as water or phenol.

As to the reaction conditions of the melt transesterification reaction, the temperature is usually in the range of 120 to 360° C., preferably in the range of 150 to 280° C., and more preferably in the range of 180 to 260° C. When the reaction temperature is too low, the transesterification reaction will not proceed, and when the reaction temperature is high, side reaction such as decomposition reaction will proceed, which are not favorable. The reaction is preferably carried out under reduced pressure, and the reaction pressure is preferably a pressure at which carbonate diester as a raw material does not distill out of the system and phenol as a by-product is distilled at the reaction temperature. Under such reaction conditions, the reaction is usually completed in about 0.5 to 10 hours.

Subsequently, the reaction product containing the aromatic polycarbonate thus obtained is subjected to a separation reduction treatment of a low molecular weight component as necessary, and then subjected to a drying step, to obtain the aromatic polycarbonate including the repeating unit represented by general formula (2) according to the present invention.

The reaction product containing the aromatic polycarbonate obtained by the above reaction step is usually a transparent viscous substance in a molten state in the vicinity of the reaction temperature, and is a solid in the vicinity of ordinary temperature.

In the separation reduction treatment of a low molecular weight component that may be carried out as necessary, for example, as described in JP H07-192310 A, an aromatic polycarbonate is dissolved in an appropriate good solvent, then precipitated in a poor solvent such as methanol to be dried, whereby the aromatic polycarbonate according to the present invention in the form of particles, powder, flakes or the like in which the low molecular weight component is reduced can be obtained.

In addition, as a more preferable method for obtaining a high molecular weight aromatic polycarbonate, preliminary polymerization is carried out in the reaction as described in JP H03-223330 A or WO 00/18822 A (first step) to obtain an aromatic polycarbonate oligomer, and the aromatic polycarbonate oligomer is subjected to solid phase polymerization or swollen solid phase polymerization in the presence of a catalyst (second step), whereby a high molecular weight aromatic polycarbonate can be obtained.

The preliminary polymerization in the first step is carried out by a melt transesterification reaction, and a bisphenol compound and a diphenyl carbonate are reacted with each other while distilling phenol in the presence of a catalyst at a temperature of 120 to 360° C., preferably 150 to 280° C., and particularly preferably at 180 to 270° C. for 0.5 to 10 hours, to obtain an aromatic polycarbonate oligomer. The aromatic polycarbonate oligomer obtained in the first step is preferably formed into a solid such as flake, powder or particles according to a known method from the viewpoint of operability in the second step.

In the second step, the above-mentioned transesterification catalyst such as a quaternary phosphonium salt is appropriately added as necessary to the aromatic polycarbonate oligomer obtained in the first step under reduced pressure, and the mixture is reacted by introducing an inert gas under stirring while distilling residual phenol at a temperature equal to or higher than the glass transition temperature of the aromatic polycarbonate and in a solid phase state or a swollen solid phase state in which the crystallized oligomer is not melted during the solid phase polymerization, to obtain a high molecular weight aromatic polycarbonate.

The reaction in the first step and the reaction in the second step may be carried out separately or in succession. Here, the aromatic polycarbonate oligomer usually generally has, for example, a weight average molecular weight of about 500 to 15,000. Further, the high molecular weight aromatic polycarbonate generally has, for example, a weight average molecular weight of about 15,000 to 100,000. However, the aromatic polycarbonate of the present invention is not limited to one having such a molecular weight.

With respect to the bisphenol compound of the present invention obtained as described above, its use and it derivatives obtained by known methods such as substitution of a phenolic hydroxyl group will also be specifically described.

For example, 3,3-bis(4-glycidyloxy-3-phenylphenyl)-1-phenyl-1H-indol-2-one or the like is obtained by reacting the bisphenol compound of the present invention with epichlorohydrin, and an epoxy resin can be obtained by using these compounds as raw materials.

3,3-Bis(4-[2-(3-oxetanyl)]butoxy-3-phenylphenyl)-1-phenyl-1H-indol-2-one or the like is obtained by reacting the bisphenol compound of the present invention with 2-(3-oxetanyl)butyl tosylate, and an oxetane resin can be obtained by using these compounds as raw materials.

3,3-Bis(4-(meth)acryloxy-3-phenylphenyl)-1-phenyl-1H-indol-2-one or the like can be obtained by reacting the bisphenol compound of the present invention with acrylic acid (or methacrylic acid), and a resin can be formed by using these compounds as raw materials.

3,3-Bis(5-hydroxymethyl-4-hydroxy-3-phenylphenyl)-1-phenyl-1H-indol-2-one or the like can be obtained by reacting the bisphenol compound of the present invention with formaldehyde. 3,3-Bis(5-methoxymethyl-4-hydroxy-3-phenylphenyl)-1-phenyl-1H-indol-2-one or the like can be obtained by reacting this methylol compound with methanol.

3,3-Bis(4-[(6-diazo-5-oxonaphthyl)sulfonyloxy]-3-phenylphenyl)-1-phenyl-1H-indol-2-one or the like can be obtained by reacting the bisphenol compound of the present invention with 1,2-naphthoquinonediazide-5-sulfonic acid chloride, and the obtained compounds can be used in a photosensitive composition.

As other uses, the compound of the present invention has a plurality of phenolic hydroxyl groups, so that besides polycarbonate, utilization as a resin raw material such as polyester, polyarylate, polyether ether ketone, polysulfone, novolac or resole, an i-line resist additive, a developer or an antioxidant can be also expected.

Also, the aromatic polycarbonate of the present invention obtained by using the bisphenol compound of the present invention as a raw material is excellent in transparency, heat resistance, mechanical properties, impact resistance, flowability and the like when the aromatic polycarbonate is made to be a high molecular weight polycarbonate. The aromatic polycarbonate of the present invention is expected to be used in various fields such as optical uses of optical lenses used in optical disks, smartphones and the like, optical films used in flat panel displays and the like, as well as automobile fields, electric and electronic fields, various containers and the like as engineering plastics.

Also, the aromatic polycarbonate oligomer can be widely used not only as a raw material in producing a high molecular weight polycarbonate by various polymerization methods but also as a polymer modifier such as a surface modifier, a flame retardant, an ultraviolet absorber, a flow modifier, a plasticizer or a solubilizing agent for a resin alloy, as well as an additive

EXAMPLES

Hereinafter, the present invention will be specifically described with reference to examples, but the present invention is not limited to these examples.

The softening point and the refractive index in the following examples were measured by the following methods. The analysis method is as follows.
<Analysis Method>
1. Softening Point Measurement
Apparatus: DSC-60 DIFFERENTIAL SCANNING CALORIMETER manufactured by Shimadzu Corporation
Temperature rise condition: 10° C./min. (30.0° C.→200° C.)
Atmosphere gas: Nitrogen gas (flow rate: 50 ml/min.)
Measurement method: The first measurement was carried out under the temperature rise condition, and the melting point was measured from the endothermic peak. Thereafter, the same sample was cooled to room temperature, the second measurement was carried out under the same conditions, and the endothermic peak was taken as the softening point.
2. Refractive Index Measurement
Apparatus: Refractometer RA-500N manufactured by KYOTO ELECTRONICS MANUFACTURING CO., LTD.
Measurement method: THF solutions (THF refractive index 1.40) at concentrations of 10, 15 and 30% were prepared, and the refractive index of the measurement compound was calculated from the refractive index of the solution by extrapolation.

Example 1

Production of 3,3-bis(4-hydroxy-3-phenylphenyl)-1-phenyl-1H-indol-2-one

Into a four-necked flask equipped with a thermometer, a stirrer, and a thermometer, 680.4 g (4.00 mol) of 2-phenylphenol and 223 g (1.00 mol) of 1-phenyl-1H-indole-2,3-dione were placed, and the air in the reaction vessel was replaced with nitrogen, after which hydrogen chloride gas was blown at 40° C., and the concentration of hydrogen chloride gas in the gas phase part was set to 95% or more. Thereafter, 22.3 g of a 15% aqueous sodium methyl mercaptan solution (0.05 mol as methyl mercaptan sodium) was added thereto, and the mixture was stirred at 40° C. for 19 hours. After the completion of the reaction, 409.4 g of a 16% aqueous sodium hydroxide solution (1.64 mol as sodium hydroxide) was added so as to adjust the pH to 5 to 6. The resulting solution was heated to 78° C., then 612.0 g of methanol was added thereto, and the obtained solution was cooled to 35° C. The precipitated crystals were separated by filtration to obtain 691.7 g of white crystals.

To the obtained white crystals were added 2026.2 g of toluene and 675.4 g of methyl ethyl ketone to dissolve, then 675.4 g of water was added thereto, and the mixture was stirred at 80° C. and allowed to stand still, then the water washing operation for extracting the water layer was repeated twice. The oil layer was heated to 107° C., and 919.3 g of the solvent was removed by distillation, then the resulting substance was cooled to 25° C., and the precipitated crystals were separated by filtration. The obtained crystals were dried under reduced pressure to obtain 417.6 g of 3,3-bis(4-hydroxy-3-phenylphenyl)-1-phenyl-1H-indol-2-one. The purity, yield and physical property values of the obtained compound are as follows.

Purity 99.0% (high performance liquid chromatography)
Yield 77% (vs 1-phenyl-1H-indole-2,3-dione)
Melting point 180° C./218° C. (differential scanning calorimetry)
Softening point 116° C. (differential scanning calorimetry)
Refractive index ($n_D20$) 1.67
Proton nuclear magnetic resonance spectrum (400 MHz, solvent DMSO-$D_6$, standard TMS)
Chemical shift (signal shape, number of protons)
6.8 ppm (d, 1H), 7.0 ppm (d, 2H), 7.1 ppm (dd, 2H), 7.2 ppm (m, 3H), 7.2 to 7.3 ppm (m, 3H), 7.4 ppm (t, 4H), 7.4 to 7.5 ppm (m, 8H), 7.5 to 7.6 ppm (m, 2H), 9.7 ppm (s, 2H)

Comparison of Physical Properties with 3,3-Bis(4-Hydroxyphenyl)-1-Phenyl-1H-indol-2-one (Compound A)

The melting point, softening point and refractive index of the compound obtained in Example 1 and "Compound A" are each listed in Table 1. The physical properties of "Compound A" were measured in the same manner as in Example 1.

TABLE 1

|  | Compound of Example 1 | Compound A |
|---|---|---|
| Melting point (° C.) | 180/218 | 297 |
| Softening point (° C.) | 116 | 117 |
| Refractive index (nD20) | 1.67 | 1.65 |

The compound of Example 1 of the present invention has a low melting point while maintaining heat resistance (softening point) as compared with the known "Compound A", thus is excellent in operability during melt polymerization in polycarbonate production, and further, in addition to high heat resistance and low melting point, the compound of Example 1 of the present invention has a high refractive index as compared with Compound A. Accordingly, it could be confirmed that the compound of Example 1 of the present invention is useful as a polycarbonate raw material for optical materials.

Example 2

Production of Polycarbonate

Into a four-necked flask equipped with a thermometer, a stirrer, and a thermometer, 65.0 g (0.12 mol) of 3,3-bis(4-hydroxy-3-phenylphenyl)-1-phenyl-1H-indol-2-one and 25.5 g (0.12 mol) of diphenyl carbonate were placed, and an aqueous cesium carbonate solution was added so that cesium carbonate was in an amount of 5 μmol per mole of 3,3-bis(4-hydroxy-3-phenylphenyl)-1-phenyl-1H-indol-2-one. The air in the reaction vessel was replaced with nitrogen, after which the pressure was reduced to 50 kPa, and the temperature was raised to 180° C. While maintaining the temperature at 180° C., the pressure was reduced to 13.3 kPa over 30 minutes, and then the temperature was raised to 200° C. While maintaining the temperature at 200° C., the pressure was reduced to 1.3 kPa over 30 minutes with distilling phenol, then the temperature was raised to 220° C., and the temperature was maintained for 1 hour. The temperature was further raised to 260° C., and the transesterification reaction was carried out for 3 hours to obtain a polymer having a weight average molecular weight (Mw) of 7100 (in terms of polystyrene) and a glass transition temperature of 187° C.

The invention claimed is:

1. A bisphenol compound represented by general formula (1) below:

[Chemical Formula 1]

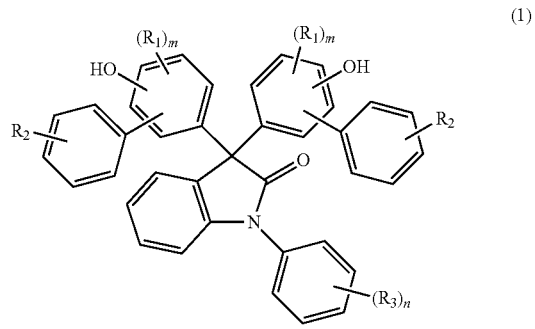

(1)

wherein $R_1$s each independently represent an alkyl group having 1 to 8 carbon atoms, an alkoxy group having 1 to 8 carbon atoms, a phenyl group or a halogen atom, $R_2$s each independently represent a hydrogen atom, an alkyl group having 1 to 8 carbon atoms, an alkoxy group having 1 to 8 carbon atoms or a halogen atom, $R_3$ represents an alkyl group having 1 to 8 carbon atoms, an alkoxy group having 1 to 8 carbon atoms or a halogen atom, m represents an integer of 0 to 2, and n represents an integer of 0 to 2, provided that when m is 2, $R_1$s may be the same as or different from each other, and when n is 2, $R_3$s may be the same as or different from each other, wherein the bisphenol compound having a chemical structure has a melting point which is lower than that of a bisphenol compound having the chemical structure without the phenyl groups to which $R_2$ is attached.

2. An aromatic polycarbonate comprising a repeating unit represented by general formula (2) below:

[Chemical Formula 2]

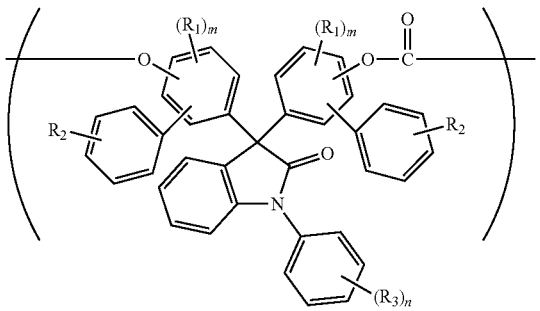

(2)

wherein $R_1$s each independently represent an alkyl group having 1 to 8 carbon atoms, an alkoxy group having 1 to 8 carbon atoms, a phenyl group or a halogen atom, $R_2$s each independently represent a hydrogen atom, an alkyl group having 1 to 8 carbon atoms, an alkoxy group having 1 to 8 carbon atoms or a halogen atom, $R_3$ represents an alkyl group having 1 to 8 carbon atoms, an alkoxy group having 1 to 8 carbon atoms or a halogen atom, m represents an integer of 0 to 2, and n represents an integer of 0 to 2, provided that when m is 2, $R_1$s may be the same as or different from each other, and when n is 2, $R_3$s may be the same as or different from each other.

3. The aromatic polycarbonate comprising the repeating unit represented by general formula (2) according to claim 2, which is obtained from the bisphenol compound represented by general formula (1) according to claim 1 and diphenyl carbonate.

\* \* \* \* \*